United States Patent
Smith

(10) Patent No.: US 8,192,353 B2
(45) Date of Patent: Jun. 5, 2012

(54) VISUAL OBTURATOR

(75) Inventor: Robert C. Smith, Middletown, CT (US)

(73) Assignee: Tyco Healthcare Group LP, Mansfield, MA (US)

( * ) Notice: Subject to any disclaimer, the term of this patent is extended or adjusted under 35 U.S.C. 154(b) by 959 days.

(21) Appl. No.: 12/194,756

(22) Filed: Aug. 20, 2008

(65) Prior Publication Data

US 2009/0093677 A1    Apr. 9, 2009

Related U.S. Application Data

(60) Provisional application No. 60/997,855, filed on Oct. 5, 2007.

(51) Int. Cl.
*A61B 1/00* (2006.01)

(52) U.S. Cl. ........ 600/114; 600/104; 600/106; 606/167; 606/170; 606/172; 606/185

(58) Field of Classification Search .................. 606/167, 606/170, 172–173, 182–185; 600/104
See application file for complete search history.

(56) References Cited

U.S. PATENT DOCUMENTS

| | | |
|---|---|---|
| 3,760,810 A | 9/1973 | Van Hoorn |
| 4,878,485 A | 11/1989 | Adair |
| 5,169,397 A | 12/1992 | Sakashita et al. |
| 5,250,068 A | 10/1993 | Ideguchi et al. |
| 5,271,380 A | 12/1993 | Riek et al. |
| 5,290,276 A | 3/1994 | Sewell, Jr. |
| 5,334,150 A | 8/1994 | Kaali |
| 5,354,302 A | 10/1994 | Ko |
| 5,376,076 A | 12/1994 | Kaali |
| 5,380,291 A | 1/1995 | Kaali |
| 5,385,572 A | 1/1995 | Nobles et al. |
| 5,431,151 A | 7/1995 | Riek et al. |
| 5,441,041 A | 8/1995 | Sauer et al. |
| 5,445,142 A | 8/1995 | Hassler, Jr. et al. |
| 5,467,762 A | 11/1995 | Sauer et al. |

(Continued)

FOREIGN PATENT DOCUMENTS

EP    0664992    8/1995

(Continued)

OTHER PUBLICATIONS

European Search Report for corresponding EP 08253194 date of mailing is Feb. 17, 2009 (3 pages).

*Primary Examiner* — Matthew J Kasztejna

(57) ABSTRACT

An obturator assembly includes a housing configured for operable engagement by a user, a sleeve mounted to the housing and extending therefrom and having a longitudinal lumen, an image passing member positioned adjacent the distal end of the sleeve and adapted to permit an optical image to pass through the image passing member and into the longitudinal lumen of the sleeve, a penetrating member adapted for longitudinal movement relative to the image passing member through a longitudinal stroke of movement to at least partially extend the penetrating member beyond the image passing member and an adjustment member operatively connected to the penetrating member. The adjustment member is movable to selectively vary a longitudinal length of the stroke of movement of the penetrating member, to thereby selectively control extension of the penetrating member relative to the image passing member. The adjustment member may also be movable to selectively vary at least one of a retracted position and an extended position of the penetrating member relative to the image passing member.

14 Claims, 13 Drawing Sheets

U.S. PATENT DOCUMENTS

| | | | |
|---|---|---|---|
| 5,551,947 A | 9/1996 | Kaali | |
| 5,562,696 A | 10/1996 | Nobles et al. | |
| 5,569,160 A | 10/1996 | Sauer et al. | |
| 5,569,291 A | 10/1996 | Privitera et al. | |
| 5,569,292 A | 10/1996 | Scwemberger et al. | |
| 5,591,192 A | 1/1997 | Privitera et al. | |
| 5,609,562 A | 3/1997 | Kaali | |
| 5,632,717 A | 5/1997 | Yoon | |
| 5,658,236 A | 8/1997 | Sauer et al. | |
| 5,658,306 A | 8/1997 | Kieturakis et al. | |
| 5,662,673 A | 9/1997 | Kieturakis | |
| 5,674,184 A | 10/1997 | Hassler, Jr. | |
| 5,685,820 A | 11/1997 | Riek et al. | |
| 5,720,761 A | 2/1998 | Kaali | |
| 5,797,944 A | 8/1998 | Nobles et al. | |
| 5,817,061 A | 10/1998 | Goodwin et al. | |
| 5,860,996 A | 1/1999 | Urban et al. | |
| 5,910,105 A * | 6/1999 | Swain et al. | 600/131 |
| 5,980,549 A | 11/1999 | Chin | |
| RE36,434 E | 12/1999 | Hamlin et al. | |
| 6,007,481 A | 12/1999 | Riek et al. | |
| 6,203,557 B1 | 3/2001 | Chin | |
| 6,206,823 B1 | 3/2001 | Kolata et al. | |
| 6,228,039 B1 * | 5/2001 | Binmoeller | 600/566 |
| 6,482,203 B2 * | 11/2002 | Paddock et al. | 606/41 |
| 6,685,630 B2 | 2/2004 | Sauer et al. | |
| 6,716,215 B1 * | 4/2004 | David et al. | 606/80 |
| 7,023,423 B2 | 4/2006 | Rosenberg | |
| 7,041,115 B2 | 5/2006 | Mirza et al. | |
| 7,074,180 B2 | 7/2006 | Bertolero et al. | |
| 7,322,933 B2 | 1/2008 | Sauer et al. | |
| 7,470,230 B2 | 12/2008 | Smith et al. | |
| 2002/0082617 A1 * | 6/2002 | Nishtala et al. | 606/139 |
| 2002/0143236 A1 | 10/2002 | Sauer et al. | |
| 2004/0015182 A1 | 1/2004 | Kieturakis et al. | |
| 2005/0065543 A1 | 3/2005 | Kahle et al. | |
| 2005/0261717 A1 | 11/2005 | Sauer et al. | |
| 2006/0079925 A1 | 4/2006 | Kerr | |
| 2006/0224174 A1 | 10/2006 | Smith et al. | |
| 2007/0016237 A1 | 1/2007 | Smith | |
| 2007/0038181 A1 * | 2/2007 | Melamud et al. | 604/158 |
| 2007/0276191 A1 | 11/2007 | Selover et al. | |
| 2008/0009894 A1 | 1/2008 | Smith | |

FOREIGN PATENT DOCUMENTS

| | | |
|---|---|---|
| EP | 0684016 | 11/1995 |
| EP | 0815796 | 1/1998 |
| EP | 1994897 | 11/2008 |
| WO | WO95/13751 | 5/1995 |
| WO | WO2004/002337 | 1/2004 |

* cited by examiner

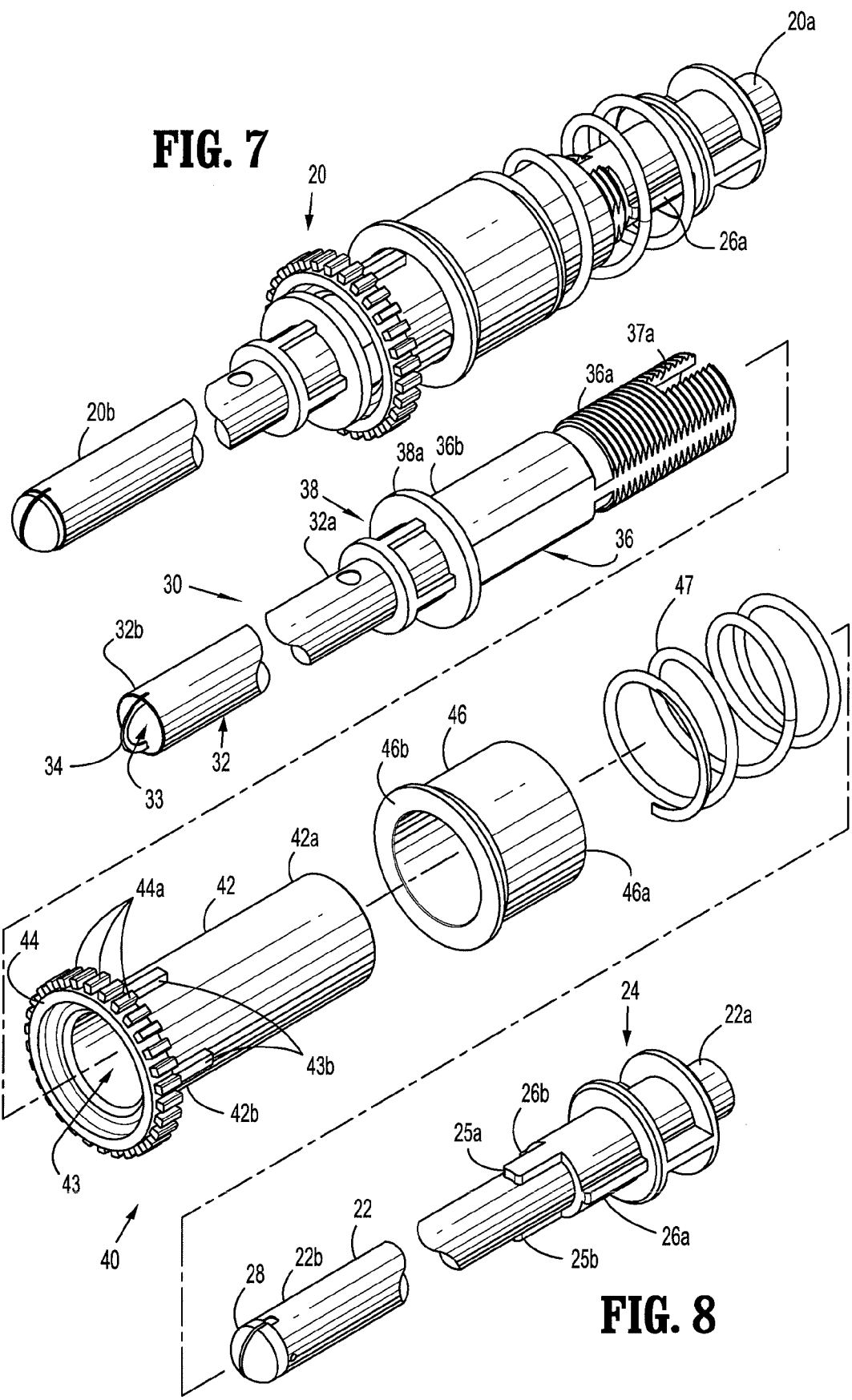

VISUAL OBTURATOR

CROSS REFERENCE TO RELATED APPLICATION

The present application claims the benefit of and priority to U.S. Provisional Application Ser. No. 60/997,855 filed on Oct. 5, 2007, the entire contents of which are incorporated herein by reference.

BACKGROUND

1. Technical Field

The present invention relates to an apparatus for penetrating and for observing penetration of body tissue. More particularly, the present invention relates to a trocar assembly configured for receiving an endoscope or laparoscope therethrough to provide visual observation during penetration of the peritoneum or other body tissue.

2. Description of the Related Art

Endoscopic surgical procedures, that is, surgical procedures performed through tubular sleeves or cannulas, have been utilized for many years. Initially, endoscopic surgical procedures were primarily diagnostic in nature. More recently as endoscopic technology has advanced, surgeons are performing increasingly complex and innovative endoscopic surgical procedures. In endoscopic procedures, surgery is performed in any hollow viscus of the body through a small incision or through narrow endoscopic tubes (cannulas) inserted through small entrance wounds in the skin. In laparoscopic procedures surgery is performed in the interior of the abdomen.

Laparoscopic procedures generally utilize instrumentation that is internally sealed to inhibit gases from entering or exiting the body through the laparoscopic or endoscopic incision. This is particularly true in surgical procedures in which the surgical region is insufflated. Moreover, laparoscopic and endoscopic procedures often require the surgeon to act on organs, tissues and vessels far removed from the incision, thereby requiring that any instruments to be used in such procedures be of sufficient size and length to permit remote operation. Typically, after the surgical region is insufflated, trocars are used to puncture the body cavity and include a cannula which remains in place for use during endoscopic procedures.

Generally, trocars used during such procedures include a stylet having a sharp tip for penetrating the body cavity positioned coaxially within protective tubes to protect a patient or surgeon from inadvertent contact with the tip. An example of a known trocar is described in commonly assigned, U.S. Pat. No. 6,685,630 to Sauer, et al, the entire contents of which are herein incorporated by reference. Sauer '630 discloses a trocar assembly for observing the penetration of the peritoneum or other body portions. The trocar assembly provides a window structure for passing optical images to an imaging system inserted into or formed within the trocar assembly, which provides a clear and bright image of the body tissue being penetrated. The assembly also includes a light pipe for passing illumination light to body tissue. The assembly may additionally include a cutting tip for penetration of body tissue.

SUMMARY

Accordingly, the present disclosure is directed to an obturator assembly including a housing configured for operable engagement by a user, a sleeve mounted to the housing and extending therefrom and having a longitudinal lumen, an image passing member positioned adjacent the distal end of the sleeve and adapted to permit an optical image to pass through the image passing member and into the longitudinal lumen of the sleeve, a penetrating member adapted for longitudinal movement relative to the image passing member through a longitudinal stroke of movement to at least partially extend the penetrating member beyond the image passing member and an adjustment member operatively connected to the penetrating member. The adjustment member is movable to selectively vary a longitudinal length of the stroke of movement of the penetrating member, to thereby selectively control extension of the penetrating member relative to the image passing member.

An elongated member may extend through the sleeve and be operatively connected to the penetrating member. The elongated member is movable to cause the penetrating member to move through the stroke of movement. The adjustment member is operatively connected to the elongated member. The adjustment member may be adapted for rotational movement relative to the longitudinal axis. The adjustment member and the elongated member may include cooperative threaded portions whereby rotation of the adjustment member causes the elongated member to translate in a longitudinal direction. The adjustment member may be mounted to the housing and be adapted to rotate relative to the housing. The housing may include an opening for accessing the adjustment member.

The obturator assembly may further include a drive member disposed within the housing and movable to drive the elongated member to cause the penetrating member to move through the stroke of movement and a trigger mechanism having a trigger and a biasing member mounted within the housing and operatively engageable with the drive member. The trigger may be operatively connected to the drive member and movable from an initial position to an actuated position to cause corresponding retracting movement of the drive member against biasing forces of the biasing member. Upon movement of the trigger to the actuated position, the drive member is released and is distally advanced in response to the biasing forces of the biasing member to advance the elongated member to cause movement of the penetrating member through the stroke of movement. A release member may be associated with the trigger and releasably engageable with the drive member to retract the drive member during movement of the trigger to the actuated position thereof. The release member is adapted to release the drive member when the trigger is at the actuated position to permit the drive member to distally advance in response to the biasing forces of the biasing member. The drive member may be normally biased to a position in operative engagement with the release member.

Also provided is an obturator assembly including a housing configured for operable engagement by a user, a sleeve mounted to the housing and extending therefrom, the sleeve defining a longitudinal axis and proximal and distal ends, and having a longitudinal lumen, an image passing member positioned adjacent the distal end of the sleeve and adapted to permit an optical image to pass through the image passing member and into the longitudinal lumen of the sleeve, a penetrating member adapted for longitudinal movement relative to the image passing member through a longitudinal stroke of movement to at least partially extend the penetrating member beyond the image passing member, and an adjustment member operatively connected to the penetrating member. The adjustment member movable to selectively vary at least one of a retracted position and an extended position of the penetrating member relative to the image passing member.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiments given below, serve to explain the principles of the disclosure, wherein:

FIG. 7 is a perspective view of an assembled obturator sleeve of the obturator assembly of FIGS. 1-6;

FIG. 8 is an exploded perspective view of the obturator sleeve of the obturator assembly of FIGS. 1-6;

DETAILED DESCRIPTION OF THE EMBODIMENTS

Figure 1:
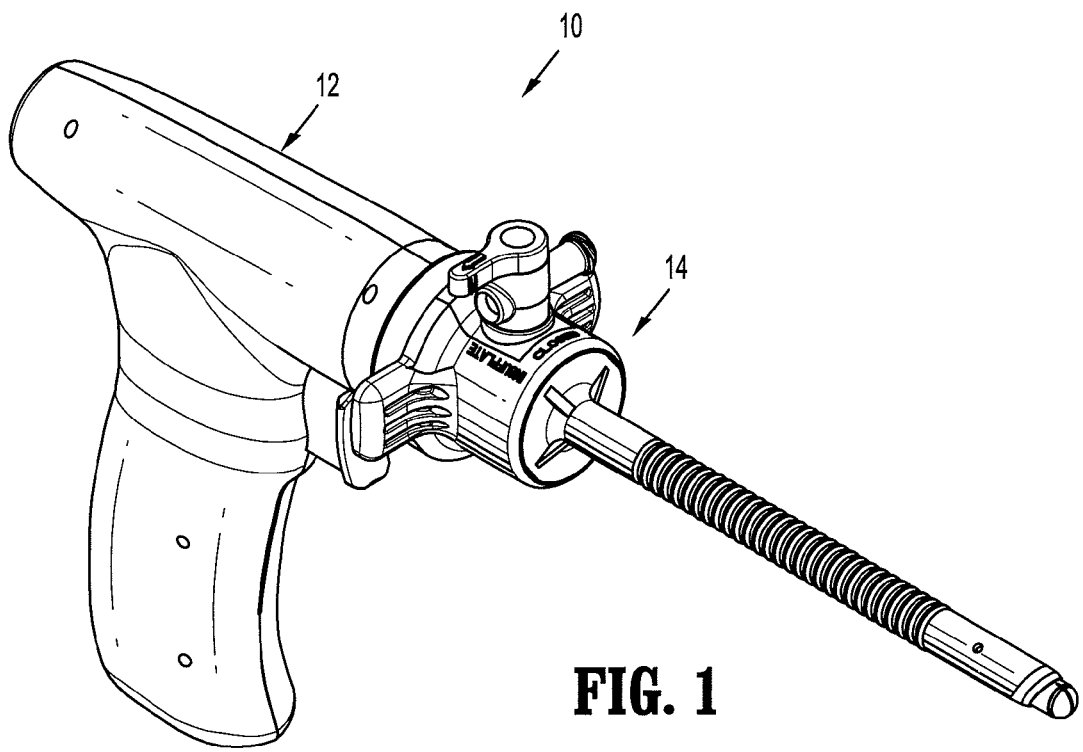
FIG. 1 is a perspective view of a trocar assembly including a cannula mounted on an obturator assembly according to an embodiment of the present disclosure.
Figure 2:
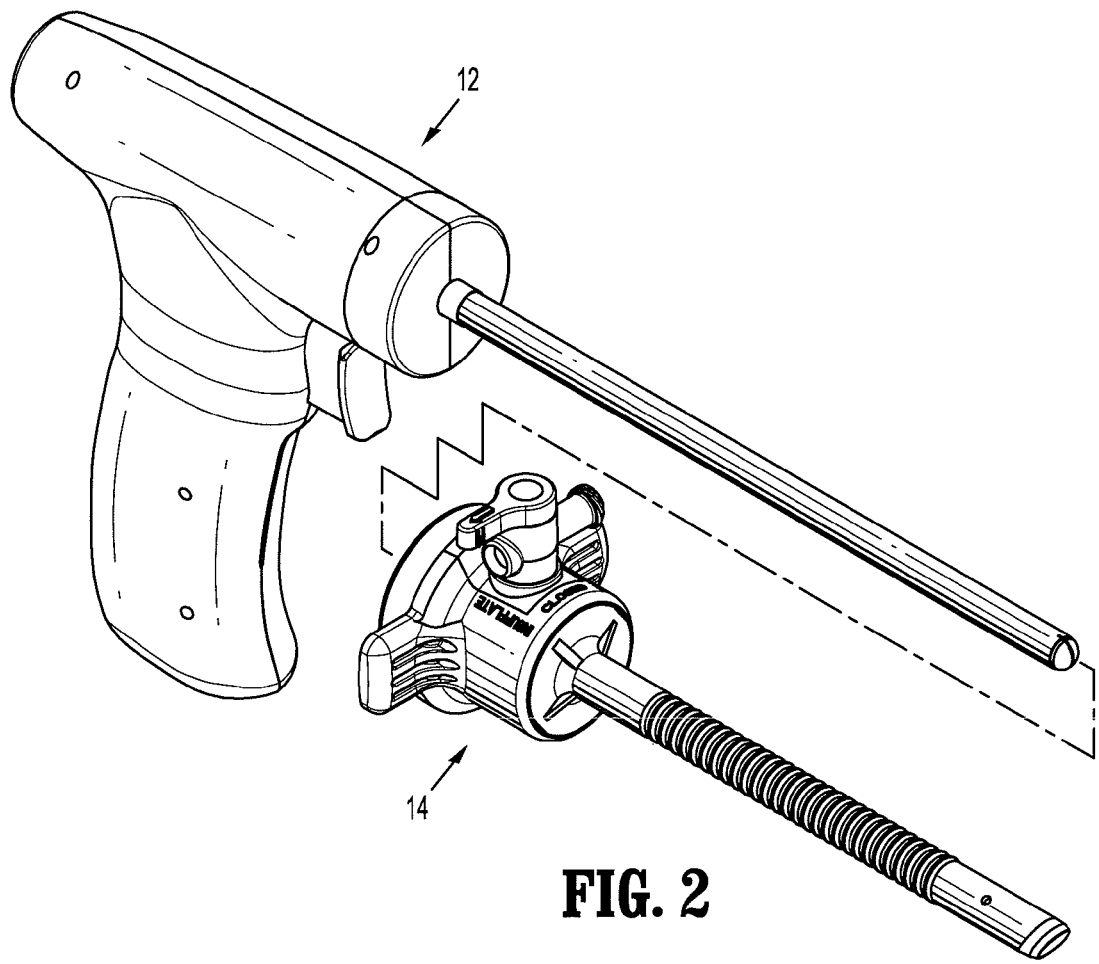
FIG. 2 is a perspective view of the trocar assembly of FIG. 1 wherein the cannula and obturator assembly are separated.

The apparatus of the present disclosure is provided to penetrate body tissue, e.g., the abdominal wall, and to provide a simultaneous forward directional view of the body tissue being penetrated. Referring initially to FIGS. 1 and 2, a trocar assembly 10 includes an obturator assembly 12 and a cannula assembly 14. As will be discussed below, trocar assembly 10 is configured to receive an endoscope (not shown) therethrough in order to provide observation of the body tissue being penetrated. Cannula assembly 14 may include any known cannula configurations capable of receiving obturator assembly 12, including cannulas having insufflation ports, release valves and the like. As used herein, the term obturator assembly refers to the tissue penetrating assembly of the trocar assembly.

Figure 4:
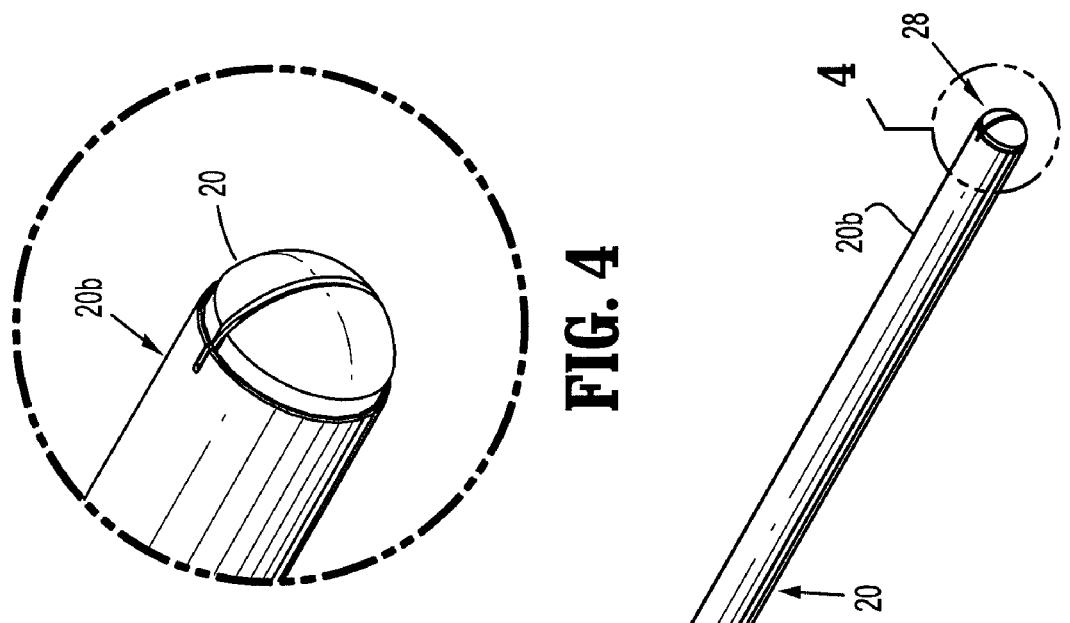
FIG. 4 is an enlarged view of portion 4 of FIG. 3.
Figure 3:
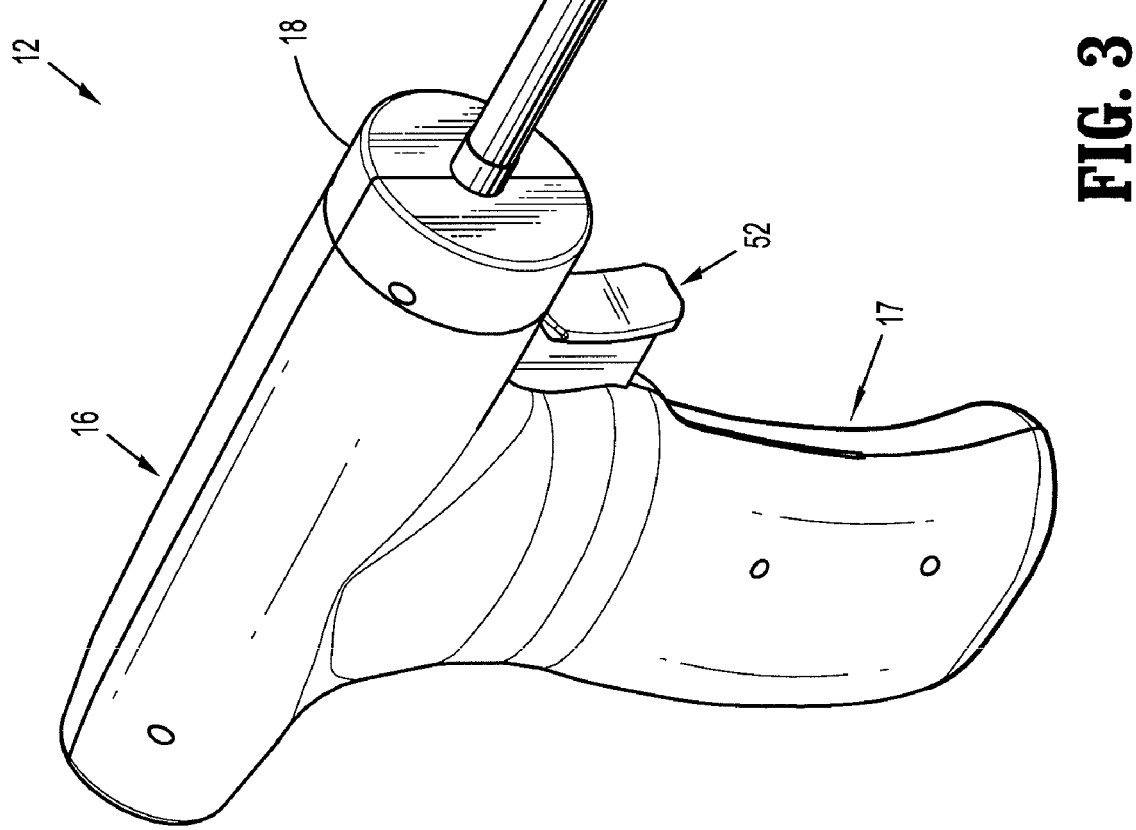
FIG. 3 is a perspective view of the obturator assembly of FIGS. 1 and 2.

Referring now to FIGS. 3 and 4, obturator assembly 12 includes housing 16 and an obturator sleeve 20 extending distally therefrom. Obturator housing 16 includes a handle 17 and a barrel portion 18. Handle 17 may be knurled, formed or otherwise configured for operable engagement by a user. Housing 16 further includes a trigger 52 operably mounted thereto and positioned for operable engagement by the user. Secured to the distal end 20b of obturator sleeve 20 is an image passing member 28.

Figure 5:
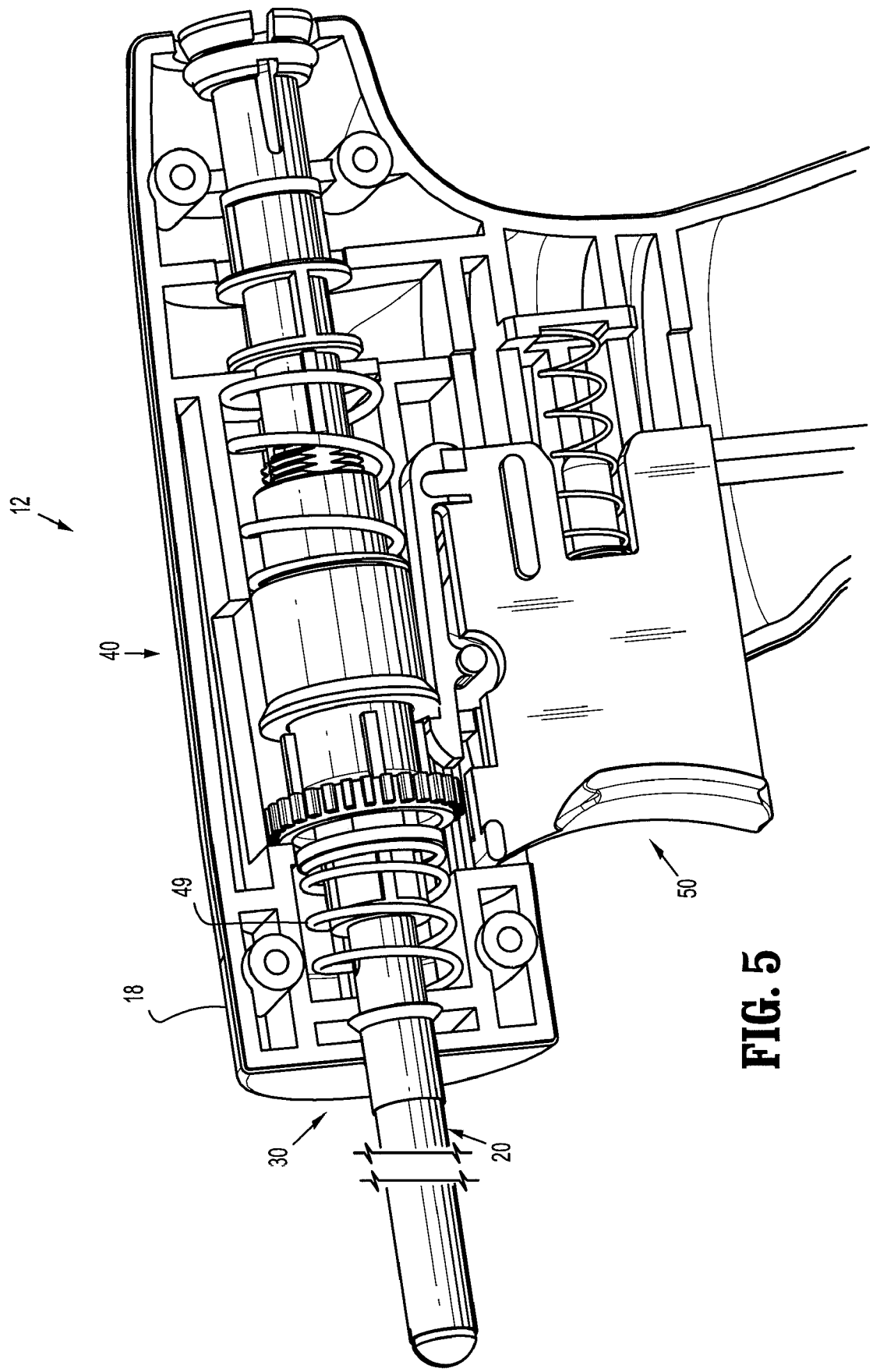
FIG. 5 is a side view of the interior of the obturator assembly of FIGS. 1-3.
Figure 13:
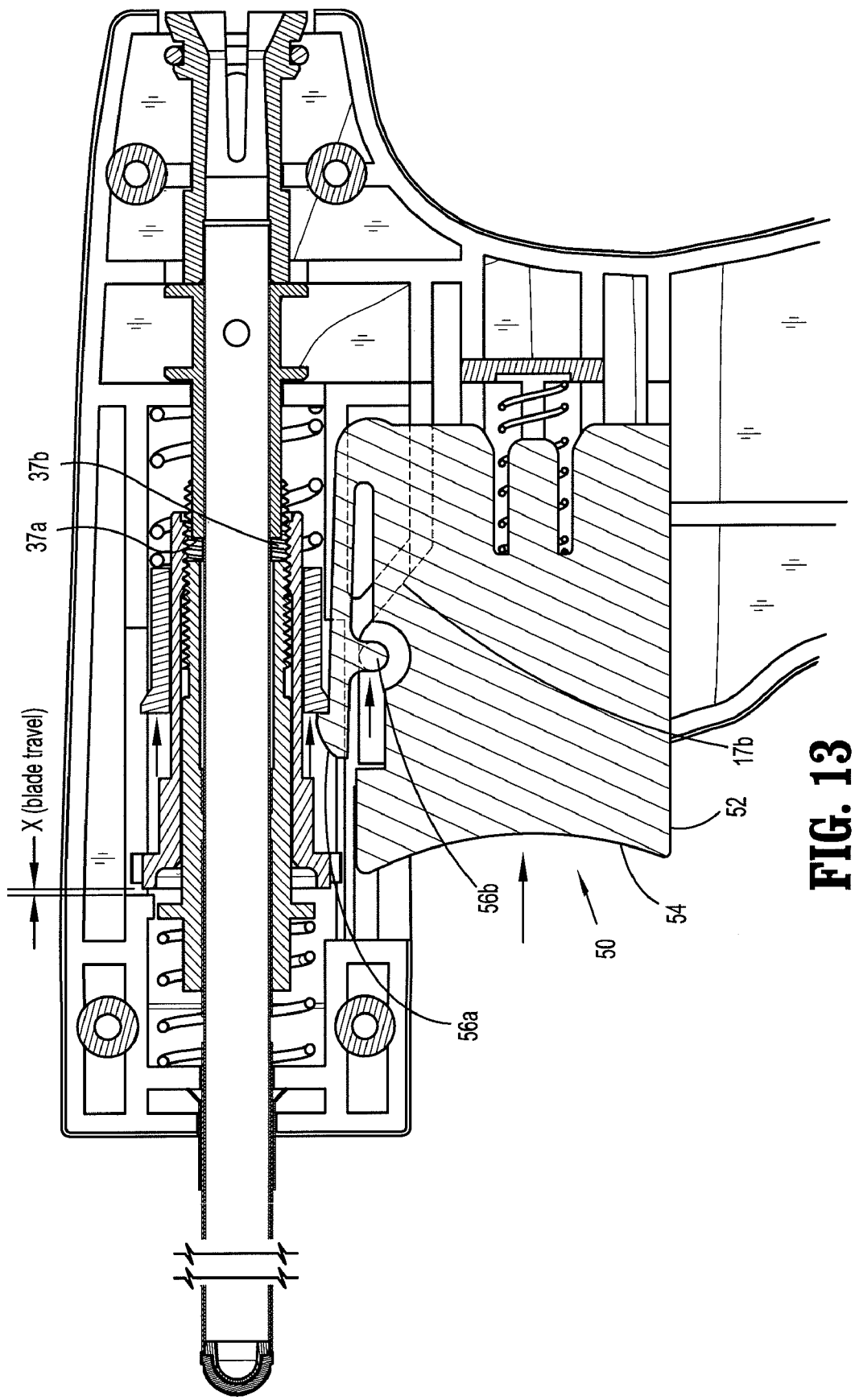
FIG. 13 is a cross-sectional side view of the obturator assembly of FIGS. 1-6 and 11, in a partially actuated condition.

Turning now to FIGS. 5-10, various views of obturator assembly 12 are shown. Referring initially to FIG. 5, an obturator sleeve 20 is slidably mounted within barrel portion 18 of obturator assembly 12. Obturator sleeve 20 includes a blade assembly 30 that is operably connected to an actuating assembly 40. A trigger assembly 50 is operably connected to actuating assembly 40 to move blade assembly 30 between a non-deployed position (FIG. 14) and a deployed position (FIG. 13).

Figure 9:
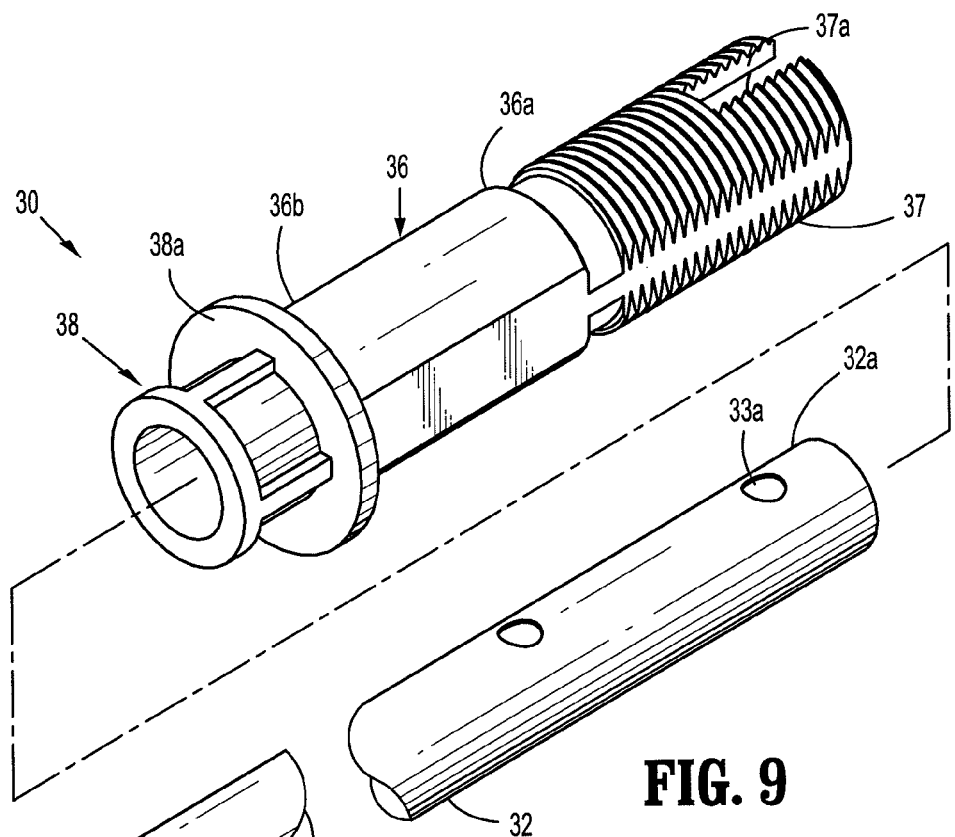
FIG. 9 is an exploded perspective view of the blade assembly of the obturator assembly of FIGS. 1-6.

With reference to FIGS. 8 and 9, blade assembly 30 includes an elongated member 32 having proximal and distal ends 32a, 32b and defining a lumen 33 therethrough. Lumen 33 is configured for receiving an endoscope therein. A cutting blade or other penetrating member 34 is mounted on distal end 32b thereof and extends distally therefrom. Cutting blade 34 may be securely affixed or selectively engageable with distal end 32b. A pusher member 36 is mounted on proximal end 32a of elongated member 32. Elongated member 32 may include one or more openings 33a for securing pusher member 36 thereto. Pusher member 36 defines a substantially annular body having proximal and distal end 36a, 36b. Proximal end 36a of pusher member 36 defines a thread portion 37. Threaded portion 37 defines notches 37a, 37b (FIG. 13). Distal end 36b of pusher member 36 defines an engagement portion 38 including a flange 38a. As will be discussed in further detail below, flange 38a is configured to engage a first spring 47.

Figure 10:
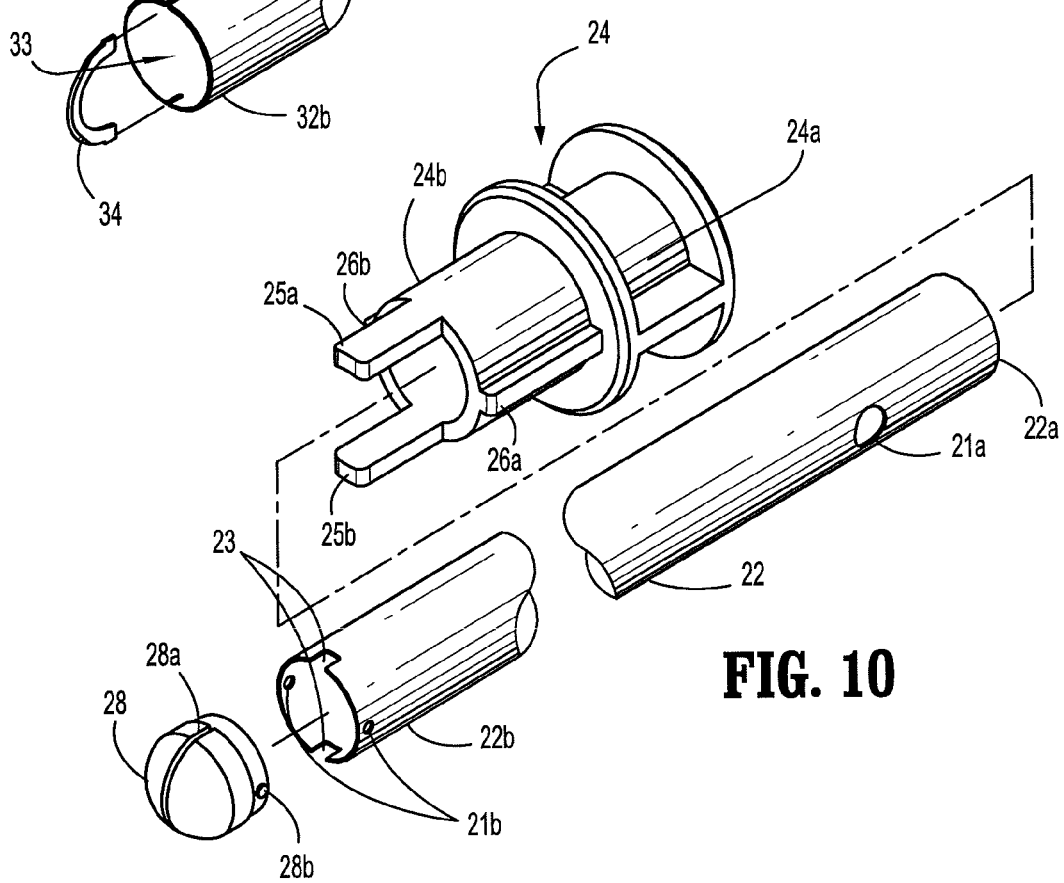
FIG. 10 is an exploded perspective view of the proximal and distal ends of the obturator sleeve of FIGS. 7 and 8.

Referring now to FIGS. 8 and 10, a mounting sleeve 22 includes proximal and distal ends 22a, 22b and defines a lumen 21 therebetween. An image passing member 28 is mounted on distal end 22b of mounting sleeve 22. Distal end 22b may define any number of openings or slots 21b configured for securing image passing member 28 thereto. Distal end 22b of mounting sleeve 22 includes notches 23 configured to permit retraction of cutting blade 34 therein. Mounted about proximal end 22a of mounting sleeve 22 is a mounting member 24. Proximal end 22a may define an opening or detent 21a for securing mounting member 24 therewith.

Figures 14, 15:
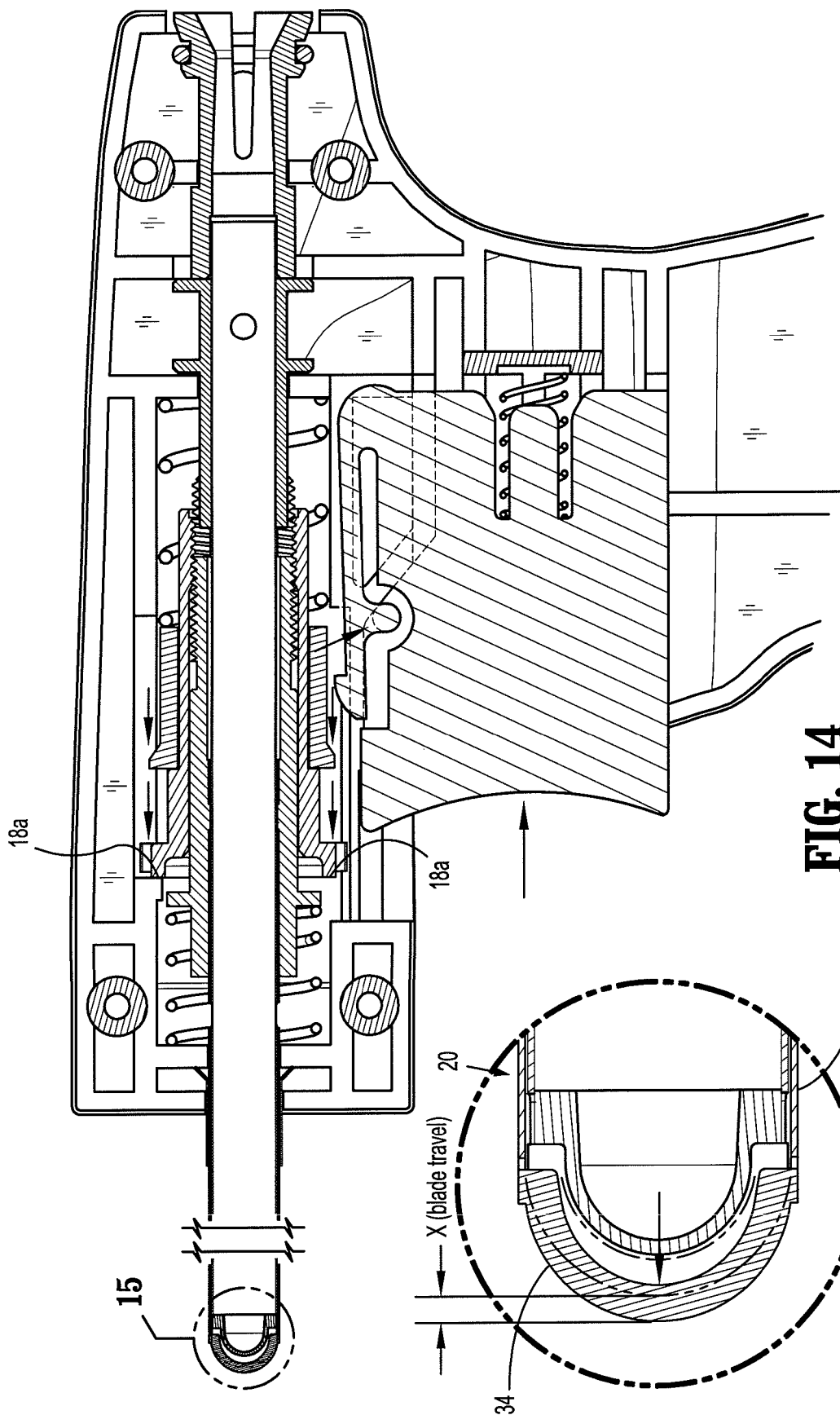
FIG. 14 is a cross-sectional side view of the obturator assembly of FIGS. 1-6, 11, and 13, in a fully actuated condition.
FIG. 15 is an enlarged view of portion 15 of FIG. 14.

Mounting member 24 defines a substantially annular member having a flanged proximal end 24a configured to be retained within barrel portion 18 of housing 16 (FIG. 14). Distal end 24b of mounting member 24 include tabs 25a, 25b extending distally therefrom. Tabs 25a, 25b are configured to be received within notches 37a, 37b, respectively, formed in threaded portion 37 of pusher assembly 36. As will be discussed below, receipt of tabs 25a, 25b of mounting member 22 within notches 37a, 37b of pusher member 36 prevents rotation of blade assembly 30. Notches 37a, 37b are sized to permit longitudinal movement of tabs 25a, 25b therein as blade assembly 30 is advanced and retracted during actuation. Distal end 24b of mounting member 24 may further include projections 26a, 26b thereon for engaging barrel portion 18 of housing 16, thereby preventing rotation of mounting member 24.

With particular reference to FIG. 10, image passing member 28 defines a transparent optical window that may be fabricated from a variety of materials such as polystyrene, polymethylmethacrylate (PMMA), polyurethane, transparent epoxies and/or glass or other transparent materials. (When made of plastic material, the cost is reduced.) Image passing member 28 may include any number of configurations. Image passing member 28 may define an image directing member, including a lens, an optical prism, an optical mirror, or like image directing medium. As shown, image passing member 28 defines a substantially dome shaped lens defining a slot 28a therein for receiving cutting blade 34 (FIG. 9). Image passing member 28 may further include tabs 28b configured to be selectively received within openings 21b formed in distal end 22b of mounting sleeve 22. Image passing member 28 may be configured to allow close to a 360° forward angle of view. Image passing member 28 may further be configured to allow for passage of illumination light from the obturator sleeve 20 to body tissue.

Figure 6:
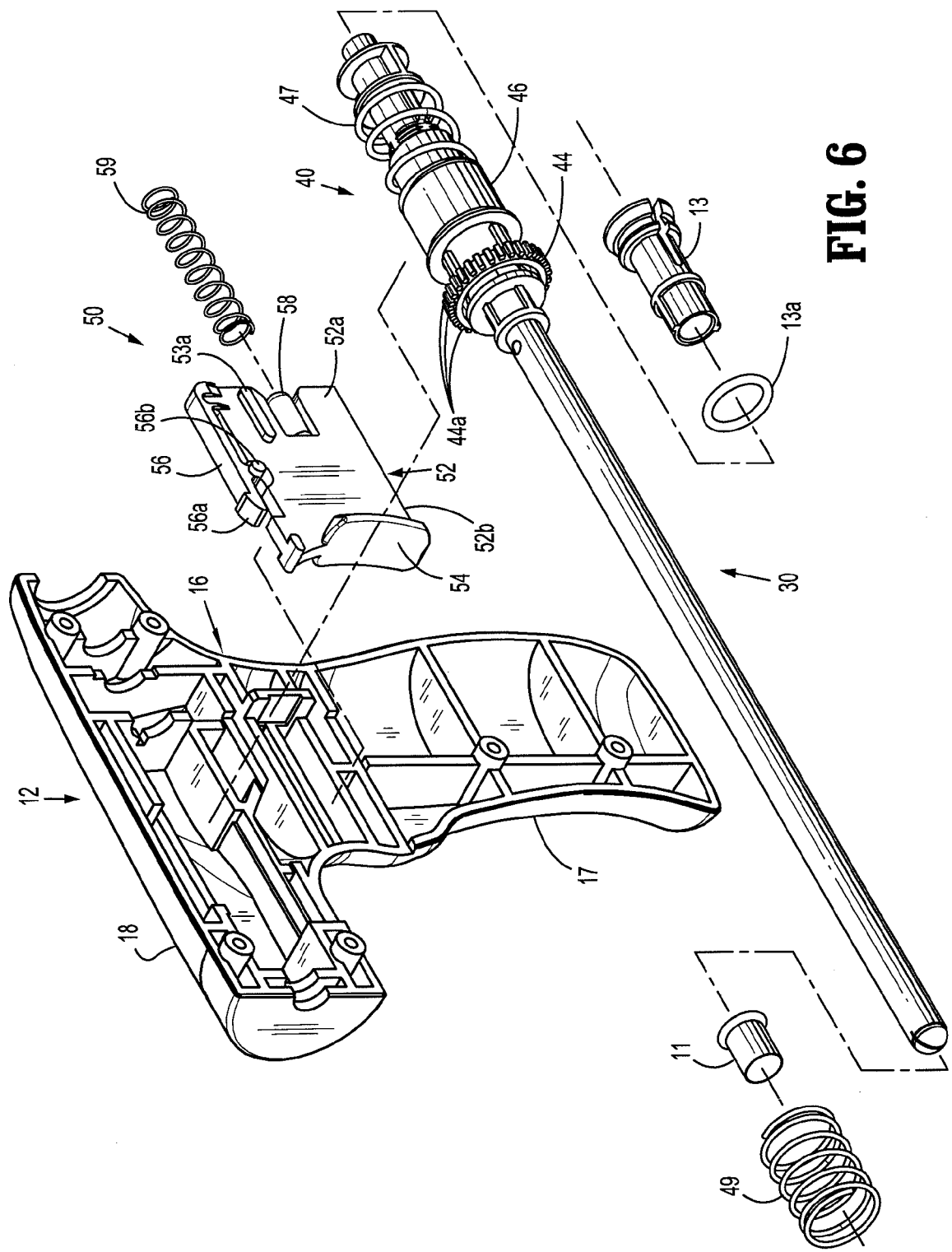
FIG. 6 is an exploded perspective view of the interior of the obturator assembly of FIGS. 1-5.
Figures 11, 12:
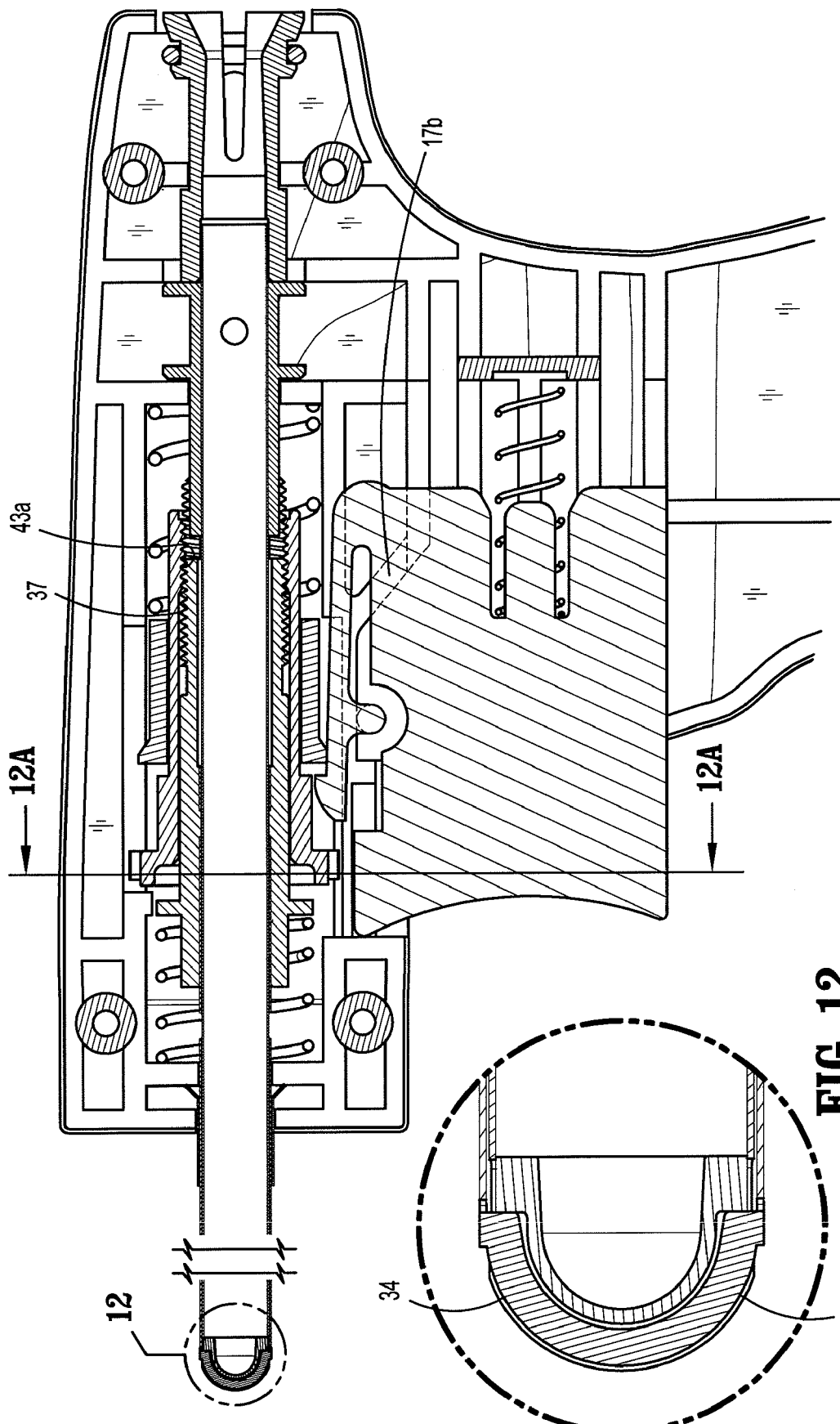
FIG. 11 is a cross-sectional side view of the obturator assembly of FIGS. 1-6.
FIG. 12 is an enlarged view of portion 12 of FIG. 11.
Figure 12A:
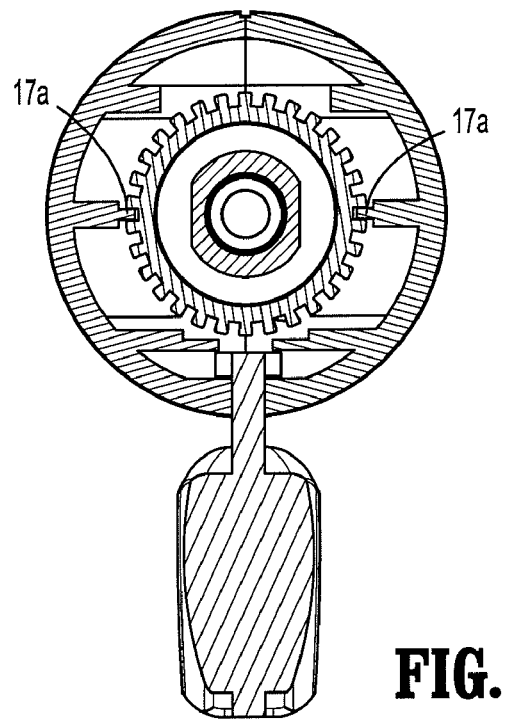
FIG. 12A is a cross-sectional end view of the obturator assembly of FIG. 12 taken along line 12A-12A.

With reference now to FIGS. 6 and 8, actuating assembly 40 includes an adjustment member 42, a hammer or other drive member 46, a first spring 47 for biasing hammer 46 during actuation, and a second spring 49 for returning blade assembly 30 to a non-deployed position (FIG. 12). Adjustment member 42 includes proximal and distal ends 42a, 42b and defines a lumen 43 therebetween. Lumen 43 is configured to receive proximal end 36a of pusher member 36. Distal end 42b of adjustment member 42 defines an adjustment nut 44. Adjustment nut 44 includes a number of protrusions 44a extending radial therefrom. As will be discussed below, protrusions 44a are configured to engage tabs 17 (FIGS. 12A and 12B) formed in housing 16 to prevent rotation of adjustment member 42 when obturator assembly 12 is fully assembled. Distal end 42b of adjustment member 42 further includes ridges 43b for engaging hammer 46. Proximal end 42a of adjustment member 42 includes an internally thread portion 43a (FIG. 14) for engaging threaded portion 37 of pusher member 36.

Still referring to FIGS. 6 and 8, hammer 46 defines a substantially annular member configured to be slidably received over the proximal end 42a of adjustment member 42. Hammer 46 includes a flanged distal end 46b configured for engaging ridges 43b formed on adjustment member 42. Hammer 46 further includes a spring engaging proximal end 46a for engaging spring 47 upon actuation of obturator assembly 12.

Figure 12B:
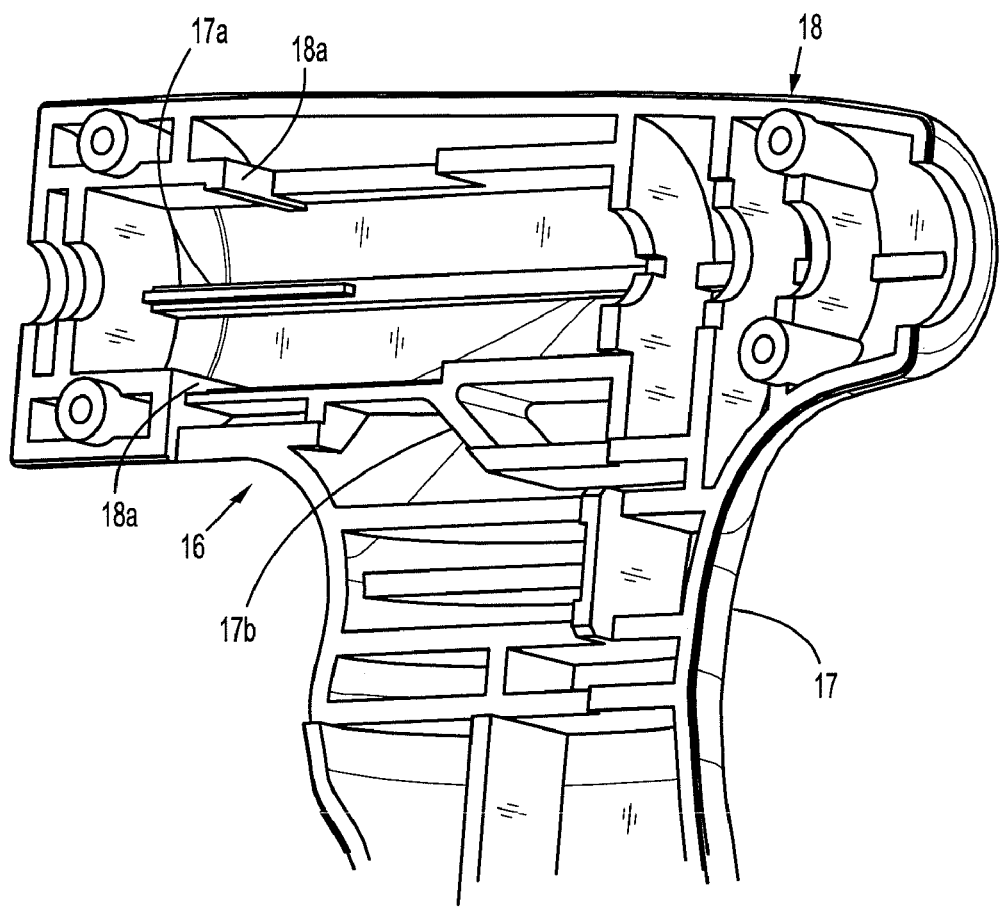
FIG. 12B is a side view of the inside of a housing half of the obturator assembly of FIGS. 1-6.

Turning back to FIGS. 5 and 6, as discussed above, trigger assembly 50 includes trigger 52 operably mounted within housing 16 of obturator assembly 12. Trigger 52 defines a substantially planar member having a finger rest 54, a hammer engaging lever 56 and a spring engagement flange 58. Trigger 52 further includes ridges 53a, 53b configured to engage housing 16 and to permit trigger 52 to be slidably received therein. Finger rest 54 is situated on a distal end 52b of trigger 52. Finger rest 54 is configured to be operably engaged by one or more fingers of a user. Proximal end 56a of hammer engaging lever 56 is mounted on a proximal end 52a of trigger 52. Lever 56 extends distally along trigger 52. Hammer engaging lever 56 includes a hammer engagement tab 56a and a ramp engagement tabs 56b. As will be discussed below, ramp engagement tabs 56b are configured to engage a ramp 17b (FIG. 12B, shown in phantom in FIGS. 11 and 13) formed in housing 16. As trigger 52 is retracted proximally, ramp engagement tab 56b engages ramp 17b. As tab 56b moves proximally along ramp 17b lever 56 is biased towards trigger 52, thereby causing the release of hammer 46. It is envisioned that trigger assembly 50 may included any suitable release member capable of retracting and releasing hammer 46. Spring engagement flange 58 is formed within proximal end 52a of trigger 52. Flange 58 is configured to engage a spring 59. Spring 59 is operably mounted between trigger 52 and housing 16 and is configured to return trigger 52 to an initial, pre-fired position following actuation of obturator assembly 12.

With particular reference now to FIG. 6, prior to final assembly of obturator assembly 12, adjustment member 42 is received over pusher assembly 36 until inner threads 43a of adjustment member 42 engage threaded portion 37 of pusher assembly 36. As will be discussed in further detail below, rotation of adjustment member 42 relative to pusher assembly 36 adjusts the position of cutting blade 34 relative to image passing member 28, thereby adjusting the length of stroke of blade assembly 30. Hammer 46 and first spring 47 may then be received over proximal end 42a of adjustment member 42. Mounting sleeve 22, including image passing member 28 and mounting member 24 mounted thereon, may then be inserted into elongated member 32 of blade assembly 30 through proximal end 32a. Upon complete insertion of mounting sleeve 22 within elongated member 32, tabs 25a, 25b formed in mounting member 24 are received within notches 37a, 37b formed in thread portion 37 of pusher member 36. As discussed above, this configuration prevents the rotation of obturator sleeve 20 relative to housing 16. In this initial condition, image passing member 28 extends beyond cutting blade 34, thereby preventing exposure of the cutting surface.

Once assembled, obturator sleeve 20 is ready to be received within housing 16. Second spring 49 is inserted over the distal end 20b of obturator sleeve 20 and is received about engagement portion 38 of pusher member 36. A bushing 11 is also received over distal end 20b of obturator sleeve 20 to center obturator sleeve 20 within barrel portion 18 of housing 16 and to reduce the friction therebetween as blade assembly 30 is actuated. Proximal end 20a of obturator sleeve 20 receives an introducer member 13 thereon, configured for receiving an endoscope, laparoscope or the like. Introducer member 13 includes a sealing ring 13a mounted on a distal end thereof for sealing the connection between introducer member 13 and mounting member 24. Referring now to FIGS. 11-15, the operation of obturator assembly will be described in detail. In a first, or initial condition (FIGS. 11 and 12), prior to squeezing of trigger 52 of trigger assembly 50, cutting blade 34 of blade assembly 30 is received within slot 28a of image passing member 28. Second spring 49 engages engagement portion 38 of pusher member 36, thereby maintaining blade assembly 30 in the retracted or initial position. Initial squeezing of trigger 52 causes hammer engaging tab 56a of hammer engaging lever 56 to engage hammer 56 (FIG. 13). Continued proximal movement of trigger 52 causes the retraction of hammer 46 relative to pusher member 36. The continued squeezing of trigger 52 also causes ramp engagement tabs 56b to engage ramps 17a formed in housing 16. Engagement of tabs 56b with ramp 17b causes hammer engaging lever 56 to be biased towards trigger 52. Ramp 17b is configured such that hammer engaging tab 56a of lever 56 biases away from hammer 46 until eventually hammer engaging tab 56a disengages hammer 46 (FIG. 14). As hammer 46 is retracted proximally along obturator sleeve 20 during the squeezing of trigger 52, first spring 45 compresses, thereby creating a biasing force acting distally on hammer 46. Upon disengagement of hammer engaging tab 56a from hammer 46, hammer 46 is rapidly urged forward. Flanged distal end 46b of hammer 46 rapidly impacts ridges 43b formed on adjustment member 42, thereby forcing adjustment member 42 distally. Stop surfaces 18a (FIG. 12B) formed in housing 16 prevent excessive distal movement of adjustment member 42.

Distal advancement of adjusting member 42 causes the distal advancement of blade assembly 30. During advancement of blade assembly 30 cutting blade 34 is exposed from within slot 28a formed in image passing member 28. The length of time cutting blade 34 is exposed or in an actuated position is limited because while blade assembly 30 is advanced, second spring 49 is compressed. Once the initial distal biasing force on blade assembly 30 has dissipated, return of second spring 49 to an uncompressed condition causes the retraction of blade assembly 30 to its retracted or initial position (FIGS. 11 and 12). The advancement of cutting blade 34 from an initial position to an actuated position and back again is referred to as the stroke of movement. Once released, spring 59 mounted between trigger 52 and housing 16 causes trigger 52 to also return to its initial position. In this manner, obturator assembly 12 is reset and ready for continued actuation.

Figure 16:
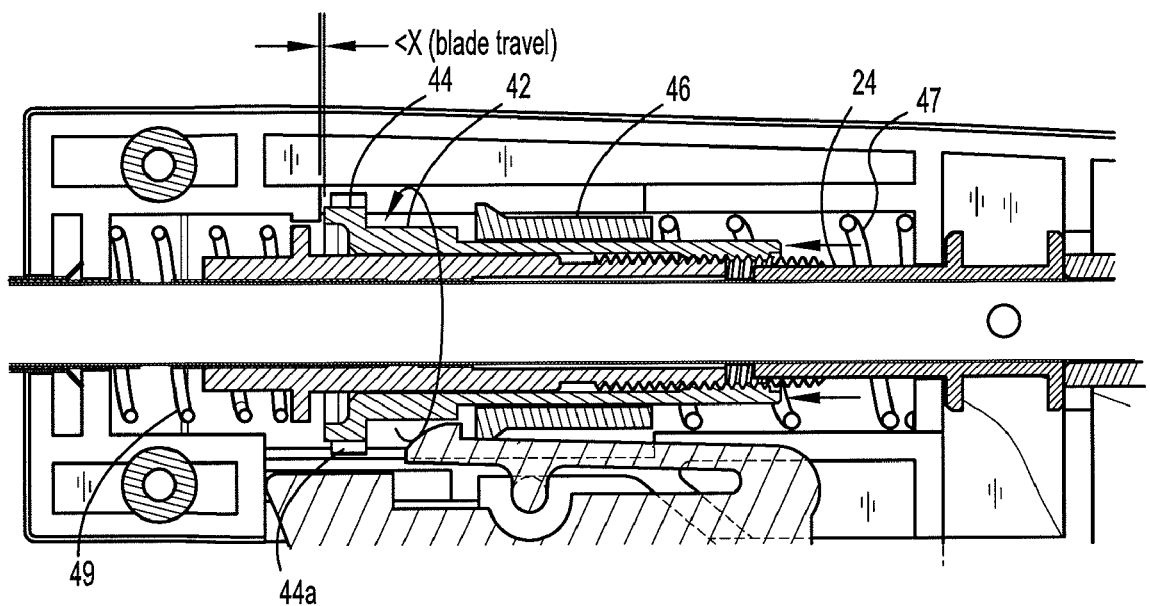
FIG. 16 a cross-sectional side view of a portion of the obturator assembly of FIGS. 1-6, 11, 13 and 14, wherein the obturator sleeve is in an adjusted position.
Figure 17:
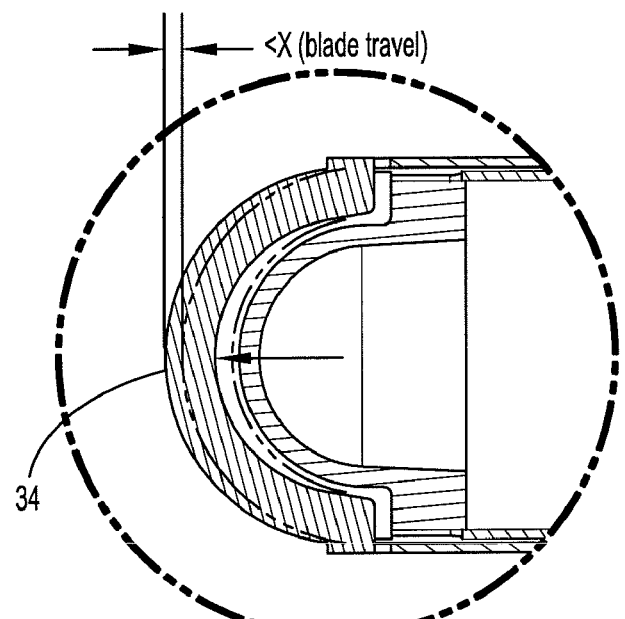
FIG. 17 is an enlarge view of a distal end of the obturator sleeve of FIG. 16.

Referring now to FIGS. 16 and 17, as briefly discussed above, the length and/or relative position of stroke of movement of cutting assembly 30 may be adjusted prior to complete assembly of obturator assembly 12, e.g., to account for different lengths of components due to manufacturing tolerances thereof. Prior to insertion within housing 16, adjustment member 42 may be rotated relative to pusher member 36. Depending on the configuration of threaded portion 37 of pusher member 36 and internal threads 43a formed on adjustment member 42, rotation of adjustment member 42 relative to pusher member 36 in a first direction causes the stroke of blade assembly 30 to increase in length, while rotation of adjustment member 42 in a second direction causes the stroke to decrease in length. In addition, adjustment obturator assembly 12 via adjustment member 42 enables precise initial positioning of the various components, e.g., cutting blade 34. In this manner, and using cutting blade 34 as an example, regardless of manufacturing tolerances, each assembled device will be assured of having cutting blade 34 be fully positioned within slot 28a when in the retracted position and extend a desired distance beyond slot 28a when in the extended position, thus providing consistent performance between different devices, which, due to manufacturing tolerance, might otherwise provide inconsistent performance relative to each other, resulting in certain devices being discarded upon testing.

Figure 18:
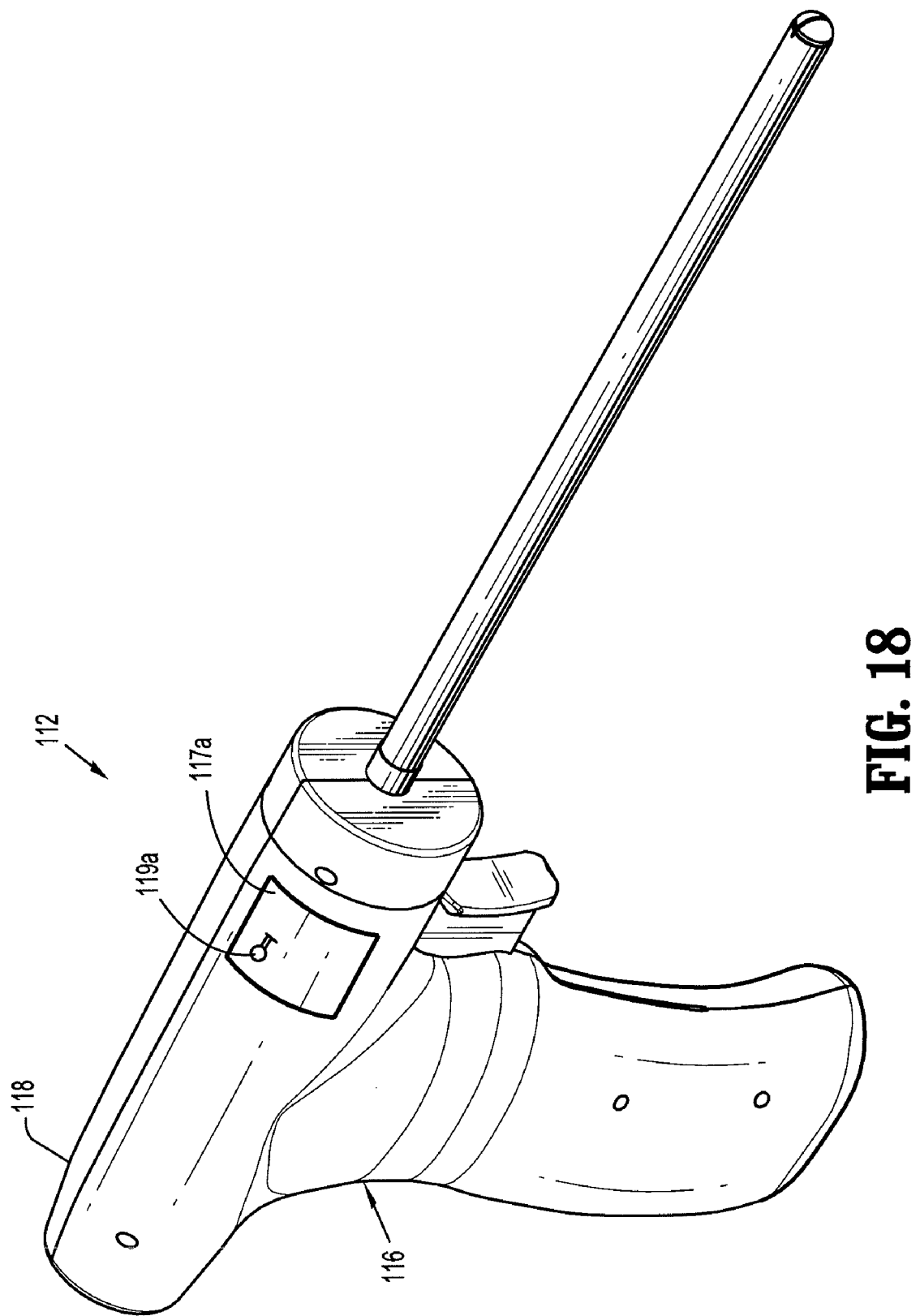
FIG. 18 is a perspective view of an alternate embodiment of the obturator assembly of the present disclosure.
Figure 19A:
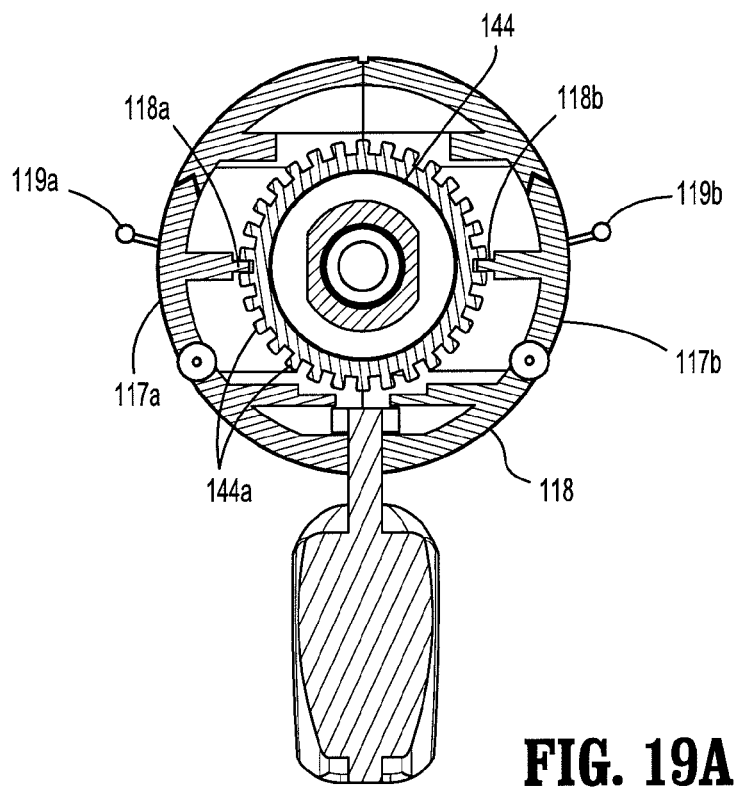
FIG. 19A is a cross-sectional end view of the obturator assembly of FIG. 18, including a housing in a closed position.
Figure 19B:
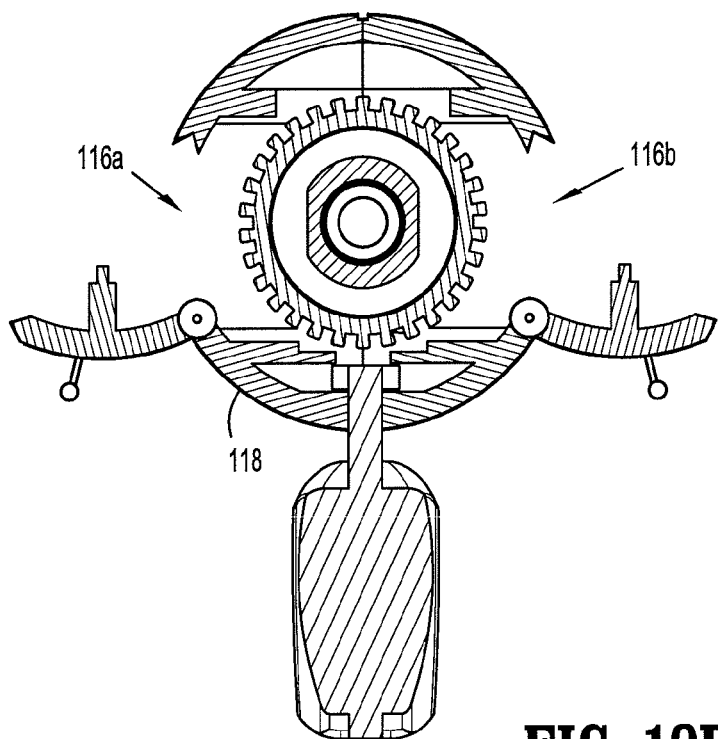
FIG. 19B is a cross-sectional end view of the obturator assembly of FIGS. 18 and 19 including the housing in an open position.

Referring now to FIGS. 18, 19A, 19B, in an alternate embodiment of the present disclosure obturator assembly 112 includes an adjustment member 142 may be rotated subsequent assembly of obturator assembly 112. Housing 116 defines a first and second opening 116a, 116b therein for accessing adjustment member 142. Housing 116 may further include doors or latches 117a, 117b for covering adjustment member 142 during actuation. Doors 117a, 117b may be pivotally mounted with housing 116. Doors 117a, 117b may include tabs 118a, 118b for engaging protrusions 144a formed on adjustment nut 144 of adjustment member 142, thereby preventing rotation of adjustment member 142 once adjustment member 142 has been rotated sufficiently to set blade assembly (not shown) to a desired stroke length. Doors 117a, 117b may also include grip members 119a, 119b for permitting a user access to adjustment member 142. With particular reference to FIGS. 19A and 19B, doors 117 may be pivotally mounted to barrel portion 118 of housing 116. It is envisioned that housing 116 may include only a single opening 116a. It is further envisioned that openings 116a, 116b be completely open and not include a door or other cover. In this manner, adjustment member 142 may be readily accessed during a procedure to adjust the length of the stroke of blade assembly 30.

It will be understood that various modifications can be made to the embodiments of the present disclosure herein disclosed without departing from the spirit and scope thereof. For example, various diameters for the cannula assembly, the obturator assembly, as well as various diameter endoscopes are contemplated. Also, various modifications may be made in the configuration of the parts. Therefore, the above description should not be construed as limiting the invention but merely as exemplifications of preferred embodiments thereof. Those skilled in the art will envision other modifications within the scope and spirit of the present disclosure as defined by the claims appended hereto.

What is claimed is:

1. An obturator assembly, which comprises: a housing configured for operable engagement by a user; a sleeve mounted to the housing and extending therefrom, the sleeve defining a longitudinal axis and proximal and distal ends, and having a longitudinal lumen; an image passing member positioned adjacent the distal end of the sleeve and adapted to permit an optical image to pass through the image passing member and into the longitudinal lumen of the sleeve; a curved cutting blade adapted for longitudinal movement relative to the image passing member through a longitudinal stroke of movement to at least partially extend the curved cutting blade beyond the image passing member; and an adjustment member operatively connected to the curved cutting blade, the adjustment member movable to selectively vary a longitudinal length of the stroke of movement of the curved cutting blade, to thereby selectively control extension of the curved cutting blade relative to the image passing member.

2. The obturator assembly according to claim 1 including an elongated member extending through the sleeve and operatively connected to the curved cutting blade, the elongated member movable to cause the curved cutting blade to move through the stroke of movement.

3. The obturator assembly according to claim 2 wherein the adjustment member is operatively connected to the elongated member.

4. The obturator assembly according to claim 3 wherein the adjustment member is adapted for rotational movement relative to the longitudinal axis.

5. The obturator assembly according to claim 4 wherein the adjustment member and the elongated member include cooperative threaded portions whereby rotation of the adjustment member causes the elongated member to translate in a longitudinal direction.

6. The obturator assembly according to claim 4 wherein the adjustment member is mounted to the housing and is adapted to rotate relative to the housing.

7. The obturator assembly according to claim 6 wherein the housing includes an opening for accessing the adjustment member.

8. The obturator assembly according to claim 2 including: a drive member disposed within the housing and movable to drive the elongated member to cause the curved cutting blade to move through the stroke of movement; and a trigger mechanism including a trigger and a biasing member mounted within the housing and operatively engageable with the drive member, the trigger operatively connected to the drive member and movable from an initial position to an actuated position to cause corresponding retracting movement of the drive member against biasing forces of the biasing member whereby, upon movement of the trigger to the actuated position, the drive member is released and is distally advanced in response to the biasing forces of the biasing member to advance the elongated member to cause movement of the curved cutting blade through the stroke of movement.

9. The obturator assembly according to claim 8 including a release member associated with the trigger and releasably engageable with the drive member to retract the drive member during movement of the trigger to the actuated position thereof, the release member releasing the drive member when the trigger is at the actuated position to permit the drive member to distally advance in response to the biasing forces of the biasing member.

10. The obturator assembly according to claim 9 wherein the drive member is normally biased to a position in operative engagement with the release member.

11. The obturator assembly according to claim 1 wherein the image passing member includes a dome-shaped lens.

12. The obturator assembly according to claim 11 wherein the dome-shaped lens defines a slot for receiving the curved cutting blade.

13. The obturator assembly according to claim 12 wherein the dome-shaped lens is configured to allow a 360° forward angle of view.

14. An obturator assembly, which comprises: a housing configured for operable engagement by a user; a sleeve mounted to the housing and extending therefrom, the sleeve defining a longitudinal axis and proximal and distal ends, and having a longitudinal lumen; an image passing member positioned adjacent the distal end of the sleeve and adapted to permit an optical image to pass through the image passing member and into the longitudinal lumen of the sleeve; a curved cutting blade adapted for longitudinal movement relative to the image passing member through a longitudinal stroke of movement to at least partially extend the curved cutting blade beyond the image passing member; and an adjustment member operatively connected to the curved cutting blade, the adjustment member movable to selectively vary at least one of a retracted position and an extended position of the curved cutting blade relative to the image passing member.

* * * * *